(12) United States Patent
Jafari et al.

(10) Patent No.: US 8,418,691 B2
(45) Date of Patent: *Apr. 16, 2013

(54) LEAK-COMPENSATED PRESSURE REGULATED VOLUME CONTROL VENTILATION

(75) Inventors: Mehdi M. Jafari, Laguna Hills, CA (US); Rhomere S. Jimenez, Winchester, CA (US); Gail F. Upham, Fallbrook, CA (US); Jeffrey K. Aviano, Escondido, CA (US)

(73) Assignee: Covidien LP, Mansfield, MA (US)

( * ) Notice: Subject to any disclaimer, the term of this patent is extended or adjusted under 35 U.S.C. 154(b) by 965 days.

This patent is subject to a terminal disclaimer.

(21) Appl. No.: 12/408,414

(22) Filed: Mar. 20, 2009

(65) Prior Publication Data

US 2010/0236555 A1 Sep. 23, 2010

(51) Int. Cl.
 *F16K 31/02* (2006.01)
(52) U.S. Cl.
 USPC ............ 128/204.21; 128/200.24; 128/204.18; 128/204.23
(58) Field of Classification Search ............. 128/200.24, 128/204.18, 204.21, 204.23
 See application file for complete search history.

(56) References Cited

U.S. PATENT DOCUMENTS

| | | | |
|---|---|---|---|
| 3,805,780 A | 4/1974 | Cramer et al. |
| 3,941,124 A | 3/1976 | Rodewald et al. |
| 4,056,098 A | 11/1977 | Michel et al. |
| 4,305,388 A | 12/1981 | Brisson |
| 4,340,044 A | 7/1982 | Levy et al. |
| 4,752,089 A | 6/1988 | Carter |
| 4,766,894 A | 8/1988 | Legrand et al. |
| 4,921,642 A | 5/1990 | LaTorraca |
| 4,939,647 A | 7/1990 | Clough et al. |
| 4,954,799 A | 9/1990 | Kumar |
| 4,971,052 A | 11/1990 | Edwards |
| 4,972,842 A | 11/1990 | Korten et al. |
| 4,986,268 A | 1/1991 | Tehrani |
| 5,057,822 A | 10/1991 | Hoffman |
| 5,072,728 A | 12/1991 | Pasternack |
| 5,072,737 A | 12/1991 | Goulding |

(Continued)

FOREIGN PATENT DOCUMENTS

| | | |
|---|---|---|
| DE | 19808543 A1 | 11/1998 |
| EP | 0425092 A | 5/1991 |

(Continued)

OTHER PUBLICATIONS

PCT, International Search Report, Date of mailing: Jun. 22, 2010, International application No. PCT/US 2010/026618 International filing date: Mar. 9, 2010, Applicant: Nellcor Puritan Bennett LLC.

(Continued)

*Primary Examiner* — Lynne Anderson
*Assistant Examiner* — Bradley Philips (57) ABSTRACT

This disclosure describes systems and methods for compensating for leakage when during delivery of gas to a patient from a medical ventilator in a pressure regulated volume control (PRVC) ventilation mode. The technology described herein includes systems and methods that compensate the delivery of PRVC ventilation for leakage in the patient circuit by using leak-compensated lung flows as well as respiratory mechanics (lung compliance and lung resistance) estimated in a manner that compensates for elastic and inelastic leaks from the ventilation system.

10 Claims, 4 Drawing Sheets

U.S. PATENT DOCUMENTS

| | | |
|---|---|---|
| 5,094,235 A | 3/1992 | Westenskow et al. |
| 5,148,802 A | 9/1992 | Sanders et al. |
| 5,150,291 A | 9/1992 | Cummings et al. |
| 5,161,525 A | 11/1992 | Kimm et al. |
| 5,237,987 A | 8/1993 | Anderson et al. |
| 5,239,995 A | 8/1993 | Estes et al. |
| 5,259,373 A | 11/1993 | Gruenke et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,313,937 A | 5/1994 | Zdrojkowski |
| 5,315,989 A | 5/1994 | Tobia |
| 5,316,009 A | 5/1994 | Yamada |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,365,922 A | 11/1994 | Raemer |
| 5,368,019 A | 11/1994 | LaTorraca |
| 5,383,449 A | 1/1995 | Forare et al. |
| 5,385,142 A | 1/1995 | Brady et al. |
| 5,388,575 A | 2/1995 | Taube |
| 5,390,666 A | 2/1995 | Kimm et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,433,193 A | 7/1995 | Sanders et al. |
| 5,438,980 A | 8/1995 | Phillips |
| 5,443,075 A | 8/1995 | Holscher |
| 5,492,113 A | 2/1996 | Estes et al. |
| 5,503,146 A | 4/1996 | Froehlich et al. |
| 5,503,147 A | 4/1996 | Bertheau |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |
| 5,542,415 A | 8/1996 | Brady |
| 5,544,674 A | 8/1996 | Kelly |
| 5,549,106 A | 8/1996 | Gruenke et al. |
| 5,551,418 A | 9/1996 | Estes et al. |
| 5,551,419 A | 9/1996 | Froehlich et al. |
| 5,555,880 A | 9/1996 | Winter et al. |
| 5,596,984 A | 1/1997 | O'Mahoney et al. |
| 5,598,838 A | 2/1997 | Servidio et al. |
| 5,605,151 A | 2/1997 | Lynn |
| 5,623,923 A | 4/1997 | Bertheau et al. |
| 5,630,411 A | 5/1997 | Holscher |
| 5,632,269 A | 5/1997 | Zdrojkowski |
| 5,632,270 A | 5/1997 | O'Mahoney et al. |
| 5,645,048 A | 7/1997 | Brodsky et al. |
| 5,645,053 A | 7/1997 | Remmers et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,685,296 A * | 11/1997 | Zdrojkowski et al. ... 128/205.24 |
| 5,687,715 A | 11/1997 | Landis et al. |
| 5,692,497 A | 12/1997 | Schnitzer et al. |
| 5,715,812 A | 2/1998 | Deighan et al. |
| 5,752,509 A | 5/1998 | Lachmann et al. |
| 5,762,480 A | 6/1998 | Adahan |
| 5,771,884 A | 6/1998 | Yarnall et al. |
| 5,791,339 A | 8/1998 | Winter |
| 5,794,615 A | 8/1998 | Estes |
| 5,794,986 A | 8/1998 | Gansel et al. |
| 5,803,065 A | 9/1998 | Zdrojkowski et al. |
| 5,813,399 A | 9/1998 | Isaza et al. |
| 5,823,187 A | 10/1998 | Estes et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,891,023 A | 4/1999 | Lynn |
| 5,901,704 A | 5/1999 | Estes et al. |
| 5,904,141 A | 5/1999 | Estes et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,927,274 A | 7/1999 | Servidio et al. |
| 5,934,274 A | 8/1999 | Merrick et al. |
| 5,970,975 A | 10/1999 | Estes et al. |
| 6,024,089 A | 2/2000 | Wallace et al. |
| 6,029,664 A | 2/2000 | Zdrojkowski et al. |
| 6,041,780 A | 3/2000 | Richard et al. |
| 6,047,860 A | 4/2000 | Sanders |
| 6,055,981 A | 5/2000 | Laswick et al. |
| 6,076,523 A | 6/2000 | Jones et al. |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,123,074 A | 9/2000 | Hete et al. |
| 6,135,106 A | 10/2000 | Dirks et al. |
| 6,142,150 A | 11/2000 | O'Mahony et al. |
| 6,148,814 A | 11/2000 | Clemmer et al. |
| 6,152,129 A | 11/2000 | Berthon-Jones |
| 6,158,432 A | 12/2000 | Biondi et al. |
| 6,161,539 A | 12/2000 | Winter |
| 6,220,245 B1 | 4/2001 | Takabayashi et al. |
| 6,223,064 B1 | 4/2001 | Lynn et al. |
| 6,253,765 B1 | 7/2001 | Högnelid et al. |
| 6,257,234 B1 * | 7/2001 | Sun .................. 128/204.18 |
| 6,269,812 B1 | 8/2001 | Wallace et al. |
| 6,273,444 B1 | 8/2001 | Power |
| 6,279,569 B1 | 8/2001 | Berthon-Jones |
| 6,283,119 B1 | 9/2001 | Bourdon |
| 6,286,508 B1 | 9/2001 | Remmers et al. |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,321,748 B1 | 11/2001 | O'Mahoney |
| 6,325,785 B1 | 12/2001 | Babkes et al. |
| 6,342,039 B1 | 1/2002 | Lynn et al. |
| 6,357,438 B1 | 3/2002 | Hansen |
| 6,360,741 B2 | 3/2002 | Truschel |
| 6,360,745 B1 | 3/2002 | Wallace et al. |
| 6,369,838 B1 | 4/2002 | Wallace et al. |
| 6,371,114 B1 | 4/2002 | Schmidt et al. |
| 6,390,091 B1 | 5/2002 | Banner et al. |
| 6,412,483 B1 | 7/2002 | Jones et al. |
| 6,425,395 B1 | 7/2002 | Brewer et al. |
| 6,427,689 B1 | 8/2002 | Estes et al. |
| 6,439,229 B1 | 8/2002 | Du et al. |
| 6,467,478 B1 | 10/2002 | Merrick et al. |
| 6,484,719 B1 | 11/2002 | Berthon-Jones |
| 6,512,938 B2 | 1/2003 | Claure et al. |
| 6,532,957 B2 | 3/2003 | Berthon-Jones |
| 6,532,958 B1 | 3/2003 | Buan et al. |
| 6,532,959 B1 | 3/2003 | Berthon-Jones |
| 6,532,960 B1 | 3/2003 | Yurko |
| 6,536,429 B1 | 3/2003 | Pavlov et al. |
| 6,536,432 B2 | 3/2003 | Truschel |
| 6,539,940 B2 | 4/2003 | Zdrojkowski et al. |
| 6,543,449 B1 | 4/2003 | Woodring et al. |
| 6,546,930 B1 | 4/2003 | Emerson et al. |
| 6,550,478 B2 | 4/2003 | Remmers et al. |
| 6,553,991 B1 | 4/2003 | Isaza |

| | | |
|---|---|---|
| 6,553,992 B1 | 4/2003 | Berthon-Jones et al. |
| 6,557,553 B1 | 5/2003 | Borrello |
| 6,561,187 B2 | 5/2003 | Schmidt et al. |
| 6,571,795 B2 | 6/2003 | Bourdon |
| 6,575,163 B1 | 6/2003 | Berthon-Jones |
| 6,578,575 B1 | 6/2003 | Jonson |
| 6,609,016 B1 | 8/2003 | Lynn |
| 6,609,517 B1 | 8/2003 | Estes et al. |
| 6,615,834 B2 | 9/2003 | Gradon et al. |
| 6,622,726 B1 | 9/2003 | Du |
| 6,626,175 B2 | 9/2003 | Jafari et al. |
| 6,629,527 B1 | 10/2003 | Estes et al. |
| 6,640,806 B2 | 11/2003 | Yurko |
| 6,644,310 B1 | 11/2003 | Delache et al. |
| 6,644,312 B2 | 11/2003 | Berthon-Jones et al. |
| 6,644,316 B2 | 11/2003 | Bowman et al. |
| 6,659,101 B2 | 12/2003 | Berthon-Jones |
| 6,668,824 B1 | 12/2003 | Isaza et al. |
| 6,671,529 B2 | 12/2003 | Claure et al. |
| 6,675,801 B2 | 1/2004 | Wallace et al. |
| 6,688,307 B2 | 2/2004 | Berthon-Jones |
| 6,701,926 B2 | 3/2004 | Olsen et al. |
| 6,718,974 B1 | 4/2004 | Moberg |
| 6,722,365 B2 | 4/2004 | Nilsson et al. |
| 6,723,055 B2 | 4/2004 | Hoffman |
| 6,723,132 B2 | 4/2004 | Salehpoor |
| 6,725,447 B1 | 4/2004 | Gilman et al. |
| 6,739,337 B2 | 5/2004 | Isaza |
| 6,748,252 B2 | 6/2004 | Lynn et al. |
| 6,752,150 B1 | 6/2004 | Remmers et al. |
| 6,752,151 B2 | 6/2004 | Hill |
| 6,755,193 B2 | 6/2004 | Berthon-Jones et al. |
| 6,758,216 B1 | 7/2004 | Berthon-Jones et al. |
| 6,760,608 B2 | 7/2004 | Lynn |
| 6,761,165 B2 | 7/2004 | Strickland, Jr. |
| 6,761,167 B1 | 7/2004 | Nadjafizadeh et al. |
| 6,761,168 B1 | 7/2004 | Nadjafizadeh et al. |
| 6,789,541 B2 | 9/2004 | Olsen et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,820,618 B2 | 11/2004 | Banner et al. |
| 6,823,866 B2 | 11/2004 | Jafari et al. |
| 6,837,242 B2 | 1/2005 | Younes |
| 6,843,250 B2 | 1/2005 | Efrati |
| 6,866,040 B1 | 3/2005 | Bourdon |
| 6,868,346 B2 | 3/2005 | Larson et al. |
| 6,874,503 B2 | 4/2005 | Rydgren |
| 6,910,480 B1 | 6/2005 | Berthon-Jones |
| 6,910,481 B2 | 6/2005 | Kimmel et al. |
| 6,920,875 B1 | 7/2005 | Hill et al. |
| 6,920,877 B2 | 7/2005 | Remmers et al. |
| 6,932,084 B2 | 8/2005 | Estes et al. |
| 6,945,248 B2 | 9/2005 | Berthon-Jones |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,986,347 B2 | 1/2006 | Hickle |
| 7,000,612 B2 * | 2/2006 | Jafari et al. ............... 128/204.21 |
| 7,008,380 B1 | 3/2006 | Rees et al. |
| 7,013,892 B2 | 3/2006 | Estes et al. |
| 7,017,576 B2 | 3/2006 | Olsen et al. |
| 7,036,504 B2 | 5/2006 | Wallace et al. |
| 7,040,320 B2 | 5/2006 | Fjeld et al. |
| 7,055,522 B2 | 6/2006 | Berthon-Jones |
| 7,066,173 B2 | 6/2006 | Banner et al. |
| 7,073,501 B2 | 7/2006 | Remmers et al. |
| 7,077,131 B2 | 7/2006 | Hansen |
| 7,081,095 B2 | 7/2006 | Lynn et al. |
| RE39,225 E | 8/2006 | Isaza et al. |
| 7,089,936 B2 | 8/2006 | Madaus et al. |
| 7,092,757 B2 | 8/2006 | Larson et al. |
| 7,100,607 B2 | 9/2006 | Zdrojkowski et al. |
| 7,100,608 B2 | 9/2006 | Brewer et al. |
| 7,100,609 B2 | 9/2006 | Berthon-Jones et al. |
| 7,107,991 B2 | 9/2006 | Kolobow |
| 7,117,438 B2 | 10/2006 | Wallace et al. |
| 7,137,389 B2 | 11/2006 | Berthon-Jones |
| 7,152,598 B2 | 12/2006 | Morris et al. |
| 7,168,429 B2 | 1/2007 | Matthews et al. |
| 7,195,028 B2 | 3/2007 | Basset et al. |
| 7,210,478 B2 | 5/2007 | Banner et al. |
| 7,229,430 B2 | 6/2007 | Hickle et al. |
| 7,267,122 B2 | 9/2007 | Hill |
| 7,270,126 B2 | 9/2007 | Wallace et al. |
| 7,275,540 B2 | 10/2007 | Bolam et al. |
| 7,296,573 B2 | 11/2007 | Estes et al. |
| 7,297,119 B2 | 11/2007 | Westbrook et al. |
| 7,331,343 B2 | 2/2008 | Schmidt et al. |
| 7,353,824 B1 | 4/2008 | Forsyth et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| 7,398,115 B2 | 7/2008 | Lynn |
| 7,406,870 B2 | 8/2008 | Seto |
| 7,428,902 B2 | 9/2008 | Du et al. |
| 7,448,381 B2 | 11/2008 | Sasaki et al. |
| 7,455,583 B2 | 11/2008 | Taya et al. |
| 7,460,959 B2 | 12/2008 | Jafari |
| 7,475,685 B2 | 1/2009 | Dietz et al. |
| 7,487,773 B2 | 2/2009 | Li |
| 7,509,957 B2 | 3/2009 | Duquette et al. |
| 7,527,056 B2 | 5/2009 | Turiello |
| 7,533,671 B2 | 5/2009 | Gonzalez et al. |
| 7,621,269 B2 | 11/2009 | Turiello |
| 7,644,713 B2 | 1/2010 | Berthon-Jones |
| 7,654,802 B2 | 2/2010 | Crawford, Jr. et al. |
| 7,661,428 B2 | 2/2010 | Berthon-Jones |
| 7,673,629 B2 | 3/2010 | Turiello |
| 7,677,247 B2 | 3/2010 | Turiello |
| 7,694,677 B2 | 4/2010 | Tang |
| 7,694,678 B2 | 4/2010 | Turiello |
| 7,717,112 B2 | 5/2010 | Sun et al. |
| 7,717,113 B2 | 5/2010 | Andrieux |
| D618,356 S | 6/2010 | Ross |
| 7,770,578 B2 | 8/2010 | Estes et al. |
| 7,784,461 B2 | 8/2010 | Figueiredo et al. |
| 7,810,496 B2 | 10/2010 | Estes et al. |
| 7,810,497 B2 | 10/2010 | Pittman et al. |
| 7,814,906 B2 | 10/2010 | Moretti |
| 7,823,588 B2 | 11/2010 | Hansen |
| 7,827,988 B2 | 11/2010 | Matthews et al. |
| 7,855,716 B2 | 12/2010 | McCreary et al. |
| 7,856,979 B2 | 12/2010 | Doshi et al. |
| D632,796 S | 2/2011 | Ross et al. |
| D632,797 S | 2/2011 | Ross et al. |
| 7,882,835 B2 | 2/2011 | Eger et al. |
| 7,886,739 B2 | 2/2011 | Soliman et al. |
| 7,886,740 B2 | 2/2011 | Thomas et al. |
| 7,891,354 B2 | 2/2011 | Farbarik |
| 7,893,560 B2 | 2/2011 | Carter |
| 7,905,231 B2 | 3/2011 | Chalvignac |
| 7,918,222 B2 | 4/2011 | Chen |
| 7,918,223 B2 | 4/2011 | Soliman et al. |
| 7,920,067 B2 | 4/2011 | Durtschi et al. |
| 7,928,852 B2 | 4/2011 | Durtschi et al. |
| D638,852 S | 5/2011 | Skidmore et al. |
| 7,934,499 B2 | 5/2011 | Berthon-Jones |
| 7,938,114 B2 | 5/2011 | Matthews et al. |
| 7,963,283 B2 | 6/2011 | Sinderby |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,002,154 B2 | 8/2011 | Fontela et al. |
| D645,158 S | 9/2011 | Sanchez et al. |
| 8,021,309 B2 | 9/2011 | Zilberg |
| 8,021,310 B2 | 9/2011 | Sanborn et al. |
| 8,033,280 B2 | 10/2011 | Heinonen |
| D649,157 S | 11/2011 | Skidmore et al. |
| 8,051,853 B2 | 11/2011 | Berthon-Jones |
| 8,070,709 B2 | 12/2011 | Childers |
| 8,083,677 B2 | 12/2011 | Rohde |
| D652,521 S | 1/2012 | Ross et al. |
| D652,936 S | 1/2012 | Ross et al. |
| 8,105,310 B2 | 1/2012 | Klein |
| D653,749 S | 2/2012 | Winter et al. |

| | | |
|---|---|---|
| 8,122,885 B2 | 2/2012 | Berthon-Jones et al. |
| D655,405 S | 3/2012 | Winter et al. |
| D655,809 S | 3/2012 | Winter et al. |
| D656,237 S | 3/2012 | Sanchez et al. |
| 8,136,521 B2 | 3/2012 | Matthews et al. |
| 8,152,116 B2 | 4/2012 | Westberg |
| RE43,398 E | 5/2012 | Honkonen et al. |
| 8,181,643 B2 | 5/2012 | Friedberg |
| 8,181,648 B2 | 5/2012 | Perine et al. |
| 8,181,649 B2 | 5/2012 | Brunner |
| 8,187,184 B2 | 5/2012 | Muller et al. |
| 8,210,173 B2 | 7/2012 | Vandine |
| 8,210,174 B2 | 7/2012 | Farbarik |
| 8,211,128 B1 | 7/2012 | Facundus et al. |
| 8,216,159 B1 | 7/2012 | Leiboff |
| 8,217,218 B2 | 7/2012 | Court et al. |
| 8,225,796 B2 | 7/2012 | Davenport et al. |
| 8,235,930 B1 | 8/2012 | McCall |
| 8,251,923 B2 | 8/2012 | Carrez et al. |
| 8,256,418 B2 | 9/2012 | Bassin |
| 8,272,379 B2 | 9/2012 | Jafari et al. |
| 8,272,380 B2 | 9/2012 | Jafari et al. |
| 8,288,607 B2 | 10/2012 | Court et al. |
| 8,302,600 B2 | 11/2012 | Andrieux et al. |
| 8,302,602 B2 | 11/2012 | Andrieux et al. |
| 2002/0014240 A1 | 2/2002 | Truschel |
| 2002/0053345 A1 | 5/2002 | Jafari et al. |
| 2002/0185126 A1 | 12/2002 | Krebs |
| 2003/0158466 A1 | 8/2003 | Lynn et al. |
| 2003/0221689 A1 | 12/2003 | Berthon-Jones |
| 2004/0074492 A1 | 4/2004 | Berthon-Jones |
| 2004/0089561 A1 | 5/2004 | Herman |
| 2004/0163648 A1 | 8/2004 | Burton |
| 2004/0187870 A1 | 9/2004 | Matthews et al. |
| 2005/0039748 A1 | 2/2005 | Andrieux |
| 2005/0109340 A1 | 5/2005 | Tehrani |
| 2005/0139212 A1 | 6/2005 | Bourdon |
| 2005/0172965 A1 | 8/2005 | Thulin |
| 2005/0188991 A1 | 9/2005 | Sun et al. |
| 2005/0241639 A1 | 11/2005 | Zilberg |
| 2006/0000475 A1 | 1/2006 | Matthews et al. |
| 2006/0011200 A1 | 1/2006 | Remmers et al. |
| 2006/0086357 A1 | 4/2006 | Soliman et al. |
| 2006/0102180 A1 | 5/2006 | Berthon-Jones |
| 2006/0112959 A1 | 6/2006 | Mechlenburg et al. |
| 2006/0118112 A1 | 6/2006 | Cattano et al. |
| 2006/0144144 A1 | 7/2006 | Seto |
| 2006/0150974 A1 | 7/2006 | Berthon-Jones |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0174883 A1 | 8/2006 | Aylsworth et al. |
| 2006/0189880 A1 | 8/2006 | Lynn et al. |
| 2006/0195041 A1 | 8/2006 | Lynn et al. |
| 2006/0201505 A1 | 9/2006 | Remmers et al. |
| 2006/0217633 A1 | 9/2006 | Glocker et al. |
| 2006/0235324 A1 | 10/2006 | Lynn |
| 2006/0241708 A1 | 10/2006 | Boute |
| 2006/0247508 A1 | 11/2006 | Fennell |
| 2006/0249150 A1 | 11/2006 | Dietz et al. |
| 2006/0249156 A1 | 11/2006 | Moretti |
| 2006/0254588 A1 | 11/2006 | Brewer et al. |
| 2006/0264762 A1 | 11/2006 | Starr |
| 2006/0272642 A1 | 12/2006 | Chalvignac |
| 2006/0278218 A1 | 12/2006 | Hoffman |
| 2007/0000494 A1 | 1/2007 | Banner et al. |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0044796 A1* | 3/2007 | Zdrojkowski et al. ... 128/204.18 |
| 2007/0068530 A1 | 3/2007 | Pacey |
| 2007/0072541 A1 | 3/2007 | Daniels, II et al. |
| 2007/0077200 A1 | 4/2007 | Baker |
| 2007/0089738 A1 | 4/2007 | Soliman et al. |
| 2007/0093721 A1 | 4/2007 | Lynn et al. |
| 2007/0101992 A1 | 5/2007 | Soliman et al. |
| 2007/0129647 A1 | 6/2007 | Lynn |
| 2007/0135736 A1 | 6/2007 | Addington et al. |
| 2007/0144522 A1 | 6/2007 | Eger et al. |
| 2007/0149860 A1 | 6/2007 | Lynn et al. |
| 2007/0157931 A1 | 7/2007 | Parker et al. |
| 2007/0163579 A1 | 7/2007 | Li et al. |
| 2007/0191688 A1 | 8/2007 | Lynn |
| 2007/0191697 A1 | 8/2007 | Lynn et al. |
| 2007/0215154 A1 | 9/2007 | Borrello |
| 2007/0221224 A1 | 9/2007 | Pittman et al. |
| 2007/0227537 A1 | 10/2007 | Bemister et al. |
| 2007/0251532 A1 | 11/2007 | Friedberg |
| 2007/0272241 A1 | 11/2007 | Sanborn et al. |
| 2007/0277823 A1 | 12/2007 | Al-Ali et al. |
| 2007/0283958 A1 | 12/2007 | Naghavi |
| 2007/0284361 A1 | 12/2007 | Nadjafizadeh et al. |
| 2008/0000478 A1 | 1/2008 | Matthiessen et al. |
| 2008/0000479 A1 | 1/2008 | Elaz et al. |
| 2008/0041382 A1 | 2/2008 | Matthews et al. |
| 2008/0041383 A1 | 2/2008 | Matthews et al. |
| 2008/0051674 A1 | 2/2008 | Davenport et al. |
| 2008/0053441 A1 | 3/2008 | Gottlib et al. |
| 2008/0053442 A1 | 3/2008 | Estes et al. |
| 2008/0053443 A1 | 3/2008 | Estes et al. |
| 2008/0053444 A1 | 3/2008 | Estes et al. |
| 2008/0066752 A1 | 3/2008 | Baker et al. |
| 2008/0066753 A1 | 3/2008 | Martin et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0168988 A1 | 7/2008 | Lu |
| 2008/0178880 A1 | 7/2008 | Christopher et al. |
| 2008/0178882 A1 | 7/2008 | Christopher et al. |
| 2008/0185002 A1 | 8/2008 | Berthon-Jones et al. |
| 2008/0200775 A1 | 8/2008 | Lynn |
| 2008/0200819 A1 | 8/2008 | Lynn et al. |
| 2008/0221469 A1 | 9/2008 | Shevchuk |
| 2008/0251079 A1 | 10/2008 | Richey |
| 2008/0295837 A1 | 12/2008 | McCormick et al. |
| 2008/0302359 A1 | 12/2008 | Loomas et al. |
| 2009/0014007 A1 | 1/2009 | Brambilla et al. |
| 2009/0050153 A1* | 2/2009 | Brunner ............ 128/204.23 |
| 2009/0082653 A1 | 3/2009 | Rohde |
| 2009/0088613 A1 | 4/2009 | Marttila et al. |
| 2009/0093697 A1 | 4/2009 | Mir et al. |
| 2009/0137927 A1 | 5/2009 | Miller |
| 2009/0149730 A1 | 6/2009 | McCrary |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0178675 A1 | 7/2009 | Turiello |
| 2009/0178676 A1 | 7/2009 | Villax et al. |
| 2009/0194100 A1 | 8/2009 | Minagi |
| 2009/0205661 A1 | 8/2009 | Stephenson et al. |
| 2009/0205663 A1 | 8/2009 | Vandine et al. |
| 2009/0229605 A1 | 9/2009 | Efrati et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0250061 A1 | 10/2009 | Marasigan |
| 2009/0281481 A1 | 11/2009 | Harding |
| 2009/0308398 A1 | 12/2009 | Ferdinand et al. |
| 2009/0314294 A1 | 12/2009 | Chalvignac |
| 2009/0318851 A1 | 12/2009 | Schenck |
| 2010/0011307 A1 | 1/2010 | Desfossez et al. |
| 2010/0018529 A1 | 1/2010 | Chalvignac |
| 2010/0024819 A1* | 2/2010 | Tiedje ............ 128/204.23 |
| 2010/0024820 A1 | 2/2010 | Bourdon |
| 2010/0065057 A1* | 3/2010 | Berthon-Jones ......... 128/204.23 |
| 2010/0071689 A1 | 3/2010 | Thiessen |
| 2010/0071695 A1 | 3/2010 | Thiessen |
| 2010/0071696 A1 | 3/2010 | Jafari |

| | | |
|---|---|---|
| 2010/0078017 A1 | 4/2010 | Andrieux et al. |
| 2010/0078018 A1 | 4/2010 | Heinonen |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0081958 A1 | 4/2010 | She |
| 2010/0101574 A1 | 4/2010 | Bassin |
| 2010/0101576 A1 | 4/2010 | Berthon-Jones |
| 2010/0116276 A1 | 5/2010 | Bayasi |
| 2010/0137737 A1 | 6/2010 | Addington et al. |
| 2010/0139660 A1 | 6/2010 | Adahan |
| 2010/0147303 A1 | 6/2010 | Jafari et al. |
| 2010/0186741 A1 | 7/2010 | Aylsworth et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0234758 A1 | 9/2010 | de Menezes |
| 2010/0236553 A1 | 9/2010 | Jafari et al. |
| 2010/0236555 A1* | 9/2010 | Jafari et al. .............. 128/204.23 |
| 2010/0252048 A1 | 10/2010 | Young et al. |
| 2010/0258123 A1 | 10/2010 | Somaiya et al. |
| 2010/0262038 A1 | 10/2010 | Tan et al. |
| 2010/0331768 A1 | 12/2010 | Hedmann et al. |
| 2011/0023879 A1 | 2/2011 | Vandine et al. |
| 2011/0034863 A1 | 2/2011 | Hoffa |
| 2011/0041850 A1 | 2/2011 | Vandine et al. |
| 2011/0061648 A1 | 3/2011 | Durtschi et al. |
| 2011/0071367 A1 | 3/2011 | Court et al. |
| 2011/0077549 A1 | 3/2011 | Kitai et al. |
| 2011/0100373 A1 | 5/2011 | Efrati et al. |
| 2011/0125052 A1 | 5/2011 | Davenport et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0178427 A1 | 7/2011 | Tan et al. |
| 2011/0196251 A1 | 8/2011 | Jourdain et al. |
| 2011/0201956 A1 | 8/2011 | Alferness et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0220112 A1 | 9/2011 | Connor |
| 2011/0226250 A1 | 9/2011 | LaBollita et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2011/0284003 A1 | 11/2011 | Douglas et al. |
| 2011/0290246 A1 | 12/2011 | Zachar |
| 2011/0293706 A1 | 12/2011 | Ludwig et al. |
| 2011/0313689 A1 | 12/2011 | Holley et al. |
| 2012/0000466 A1 | 1/2012 | Rapoport |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0006328 A1 | 1/2012 | Berthon-Jones |
| 2012/0022441 A1 | 1/2012 | Kelly et al. |
| 2012/0029317 A1 | 2/2012 | Doyle et al. |
| 2012/0030611 A1 | 2/2012 | Skidmore |
| 2012/0060835 A1 | 3/2012 | Mashak |
| 2012/0060841 A1 | 3/2012 | Crawford, Jr. et al. |
| 2012/0065533 A1 | 3/2012 | Carrillo, Jr. et al. |
| 2012/0071729 A1 | 3/2012 | Doyle et al. |
| 2012/0083729 A1 | 4/2012 | Childers |
| 2012/0090610 A1 | 4/2012 | O'Connor et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0139734 A1 | 6/2012 | Olde et al. |
| 2012/0150057 A1 | 6/2012 | Mantri |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0215081 A1 | 8/2012 | Euliano et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0304997 A1 | 12/2012 | Jafari et al. |

FOREIGN PATENT DOCUMENTS

| | | |
|---|---|---|
| EP | 1270036 A2 | 1/2003 |
| WO | WO 94/23780 A | 10/1994 |
| WO | WO 98/06449 A | 2/1998 |
| WO | WO 00/10634 A | 3/2000 |
| WO | WO 00/45880 A | 8/2000 |
| WO | WO 01/74430 A | 10/2001 |
| WO | WO 02/28460 A | 4/2002 |
| WO | WO 03/055552 A1 | 7/2003 |
| WO | WO 04000114 | 12/2003 |
| WO | WO 2004/084980 A | 10/2004 |
| WO | 2005105189 A1 | 11/2005 |
| WO | WO 2005/105189 | 11/2005 |
| WO | WO 2006/137784 A1 | 12/2006 |
| WO | WO 2006137784 A1 * | 12/2006 |
| WO | WO 2007145948 | 12/2007 |
| WO | WO 2009123981 | 10/2009 |

OTHER PUBLICATIONS

International Search Report in PCT/US10/26618 mailed on Jun. 22, 2010.
PCT International Search Report and Written Opinion in Application PCT/2009/038810, mailed Jul. 6, 2009, 16 pgs.
PCT International Search Report and Written Opinion in Application PCT/2009/038815, mailed Jul. 1, 2009, 14 pgs.
PCT International Search Report and Written Opinion in Application PCT/US09/038811, mailed Jun. 7, 2009, 13 pgs.
PCT International Search Report and Written Opinion in Application PCT/US2009/038819, mailed Jun. 26, 2009, 12 pgs.
PCT International Search Report and Written Opinion in Application PCT/US2009/038820, mailed Jul. 22, 2009, 14 pgs.
PCT International Search Report and Written Opinion in Application PCT/US2009038818, mailed Jul. 14, 2009, 15 pgs.
PCT International Search Report and Written Opinion in Application PCT/US2010/025485, mailed Feb. 27, 2009, 8 pgs.
U.S. Appl. No. 12/242,741, Notice of Allowance mailed Jun. 5, 2012, 5 pgs.
U.S. Appl. No. 12/242,741, Office Action mailed Jan. 10, 2012, 7 pgs.
U.S. Appl. No. 12/242,756, Notice of Allowance mailed Jun. 5, 2012, 5 pgs.

U.S. Appl. No. 12/242,756, Office Action mailed Jan. 10, 2012, 7 pgs.
U.S. Appl. No. 12/334,354, Notice of Allowance mailed Jan. 27, 2012, 7 pgs.
U.S. Appl. No. 12/408,408, Notice of Allowance mailed Jun. 4, 2012, 10 pgs.
U.S. Appl. No. 12/414,419, Office Action mailed Jan. 20, 2012, 15 pgs.
U.S. Appl. No. 12/414,419, Office Action mailed Jul. 18, 2012, 16 pgs.
U.S. Appl. No. 12/242,756, Supplemental Notice of Allowability mailed Aug. 27, 2012, 2 pgs.
U.S. Appl. No. 12/242,741, Supplemental Notice of Allowability mailed Aug. 27, 2012, 2 pgs.
U.S. Appl. No. 12/414,419, Amendment and Response filed Aug. 27, 2012, 8 pgs.
U.S. Appl. No. 12/334,354, Notice of Allowance mailed Oct. 5, 2012, 5 pgs.
U.S. Appl. No. 12/395,332, Office Action mailed Sep. 13, 2012, 9 pgs.
U.S. Appl. No. 13/565,595, Notice of Allowance mailed Nov. 2, 2012, 12 pgs.
U.S. Appl. No. 12/414,419, Notice of Allowance mailed Sep. 19, 2012, 8 pgs.
Jafari, M. et al., "Robust Feedback Design for Proportional Assist Ventilation—System Dynamics and Problem Definition" Decision and Control, 2005 and 2005 European Control Conference. CDC-ECC '05. 44th IEEE Conference on Seville, Spain Dec. 12-15, 2005, pp. 4839-4844, XP010884460 DISBN: 978-0-7803-9567-1, the whole document.
U.S. Appl. No. 12/238,248, Office Action mailed Oct. 15, 2012, 12 pgs.
U.S. Appl. No. 12/238,248, Office Action mailed May 14, 2012, 12 pgs.
U.S. Appl. No. 12/395,332, Notice of Allowance mailed Dec. 24, 2012, 8 pgs.
U.S. Appl. No. 12/414,419, Notice of Allowance mailed Jan. 8, 2013, 7 pgs.
U.S. Appl. No. 12/238,248, Advisory Action mailed Jan. 4, 2013, 3 pgs.
U.S. Appl. No. 13/565,595, Notice of Allowance mailed Feb. 25, 2013, 8 pgs.

* cited by examiner

FIG. 5

LEAK-COMPENSATED PRESSURE REGULATED VOLUME CONTROL VENTILATION

INTRODUCTION

In mechanical ventilation, pressure regulated volume control (PRVC) ventilation is a type of pressure regulated treatment that provides the capability to control the volume of gas delivered to the patient's lungs by adjusting the inspiratory target pressure. In PRVC, a selected volume is delivered to a patient by changing the pressure of the respiratory gas. During PRVC ventilation, the ventilator will evaluate the volume delivered to the patient and compare it against the desired volume set by the therapist. If delivered volume is less than the desired, therapist-selected volume, then the target pressure for the next breath will be increased proportionally. On the other hand, if the delivered volume exceeded the desired volume, the target pressure will be lowered.

In one implementation of PRVC, the ventilator estimates the compliance of the patient's lungs and uses the estimated lung compliance to calculate the target pressure that will result in the delivery of the pre-selected volume of gas. The magnitude and shape of the inspiratory flow delivered by the ventilator will be a function of the patient lung characteristics, breathing pattern, and other ventilator settings.

The lung compliance and lung resistance of a patient may be collectively referred to as the respiratory mechanics of the lung or, simply, the patient's respiratory mechanics. Because PRVC relies on the patient's respiratory mechanics when determining what pressure to provide for each breath, more accurate determination of respiratory mechanics is essential to performance of the ventilator when providing PRVC ventilation.

Leak-Compensated Pressure Regulated Volume Control Ventilation

This disclosure describes systems and methods for compensating for leakage when during delivery of gas to a patient from a medical ventilator in a pressure regulated volume control (PRVC) ventilation mode. The technology described herein includes systems and methods that compensate the delivery of PRVC ventilation for leakage in the patient circuit by using leak-compensated lung flows as well as respiratory mechanics (lung compliance and lung resistance) estimated in a manner that compensates for elastic and inelastic leaks from the ventilation system.

In part, this disclosure describes a method of compensating for leakage in a ventilation system during delivery of pressure regulated volume control ventilation to a patient. The method starts with monitoring an instantaneous flow of respiratory gas in the ventilation system based on one or more measurements of pressure and flow in ventilation system. Leakage of gas from the system is modeled as a first leakage component through a first orifice of a fixed size and a second leakage component through a second orifice of a varying size, in which the first and second leakage components are different functions of instantaneous pressure in the ventilation system. A leak-compensated delivered lung volume is then estimated for at least one breath based on the one or more measurements, the first leakage component and the second leakage component. The leak-compensated delivered lung volume and a predetermined respiratory mechanics model are then used to estimate a leak-compensated lung compliance. A target pressure to be delivered to the patient for a subsequent pressure-based breath is then calculated based on a desired lung volume, the leak-compensated delivered lung volume and the leak-compensated lung compliance. The target pressure is then delivered to the patient during the inspiratory phase of the next breath. The leak-compensated lung compliance may be estimated based on the leak-compensated delivered lung volume and a pressure difference, such as the difference between an end inspiratory pressure of a first breath and an end expiratory pressure of the first breath.

The disclosure also describes a method of compensating for leakage in a ventilation tubing system during delivery of gas from a medical ventilator to a patient. The method includes measuring leakage from the ventilation tubing system during a first breath and calculating a leak-compensated delivered lung volume for the first breath based on the leakage. The method then estimates a lung compliance of the patient based on the leak-compensated delivered lung volume and pressure measurements taken during the first breath. Ventilation is then delivered to the patient in a second breath at a pressure determined based on a desired delivered lung volume, the leak-compensated delivered lung volume and the leak-compensated lung compliance. As part of measuring the leakage, the method may include identifying an inelastic leakage from the ventilation tubing system as a first function of at least one of a pressure measurement and a flow measurement in the ventilation system and identifying an elastic leakage from the ventilation tubing system as a second function of at least one of the pressure measurement and the flow measurement in the ventilation system.

The disclosure further describes a pressure support system, such as a respiratory ventilator. The system includes: a pressure generating system adapted to generate a flow of breathing gas; a ventilation tubing system including a patient interface device for connecting the pressure generating system to a patient; one or more sensors operatively coupled to the pressure generating system or the ventilation tubing system, in which each sensor is capable of generating an output indicative of a pressure or flow of the breathing gas in the ventilation tubing system; a leak estimation module that identifies leakage in the ventilation tubing system; a delivered lung volume module that calculates a leak-compensated delivered lung volume for a first breath based on the leakage during the first breath and the flow of the breathing gas in the ventilation tubing system; a respiratory mechanics calculation module that generates a leak-compensated lung compliance based on the leak-compensated delivered lung volume and at least one output indicative of a pressure of the breathing gas during the first breath; and a pressure control module that causes the pressure generating system to deliver a second breath to the patient at a target pressure calculated based on the leak-compensated lung compliance and the leak-compensated delivered lung volume.

The disclosure also describes a controller for a medical ventilator that includes a microprocessor a module (which may be a software program executed by the microprocessor, or a component comprising software, hardware and/or firmware that is separate from the microprocessor) that calculates leak-compensated delivered lung volume and leak-compensated lung compliance based on instantaneous elastic leakage and instantaneous inelastic leakage of breathing gas from a ventilation system, and a pressure control module that provides pressure regulated volume control ventilation at a pressure determined based on the leak-compensated delivered lung volume and the leak-compensated lung compliance.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of medical devices, the present disclosure will discuss the implementation of these techniques in the context of a medical ventilator providing pressure regulated volume control (PRVC) ventilation to a human patient. The reader will understand that the technology described in the context of a medical ventilator for human patients could be adapted for use with other systems such as ventilators for non-human patients and general gas transport systems in which leaks may cause a degradation of performance.

In PRVC ventilation, a ventilator may evaluate the volume delivered to the patient over a breath or a specified time period and compare it against the volume set by the therapist. If the delivered volume is less than the setting, then the pressure target is increased proportionally.

Figure 1:
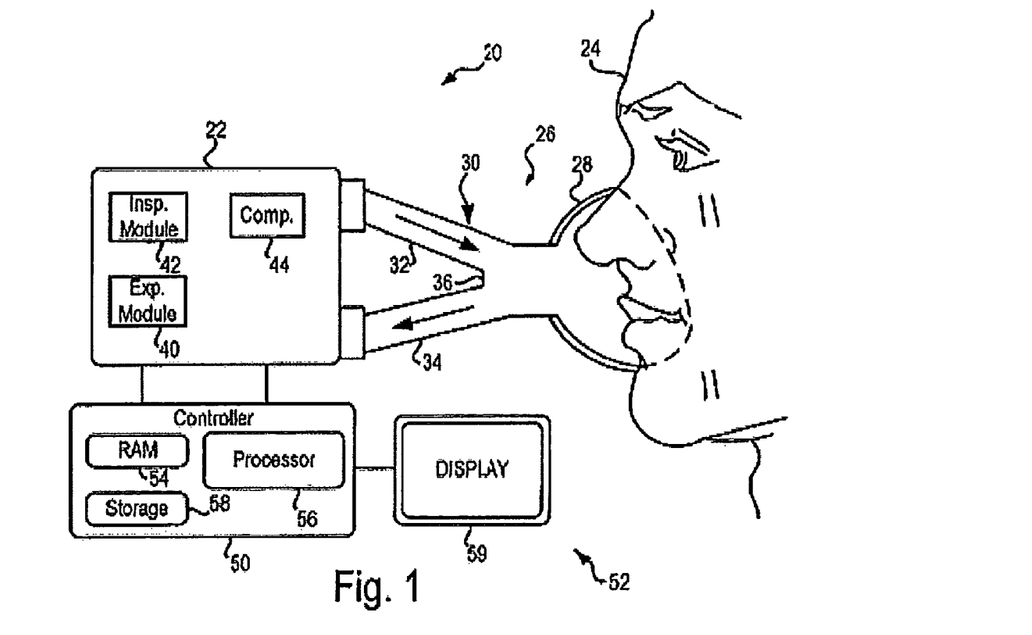
FIG. 1 illustrates an embodiment of a ventilator connected to a human patient.

FIG. 1 illustrates an embodiment of a ventilator 20 connected to a human patient 24 that is adapted to provide PRVC ventilation. Ventilator 20 includes a pneumatic system 22 (also referred to as a pressure generating system 22) for circulating breathing gases to and from patient 24 via the ventilation tubing system 26, which couples the patient to the pneumatic system via physical patient interface 28 and ventilator circuit 30. Ventilator circuit 30 could be a dual-limb or single-limb circuit for carrying gas to and from the patient. In a dual-limb embodiment as shown, a wye fitting 36 may be provided as shown to couple the patient interface 28 to the inspiratory limb 32 and the expiratory limb 34 of the circuit 30.

The present systems and methods have proved particularly advantageous in noninvasive settings, such as with facial breathing masks, as those settings typically are more susceptible to leaks. However, leaks do occur in a variety of settings, and the present description contemplates that the patient interface may be invasive or non-invasive, and of any configuration suitable for communicating a flow of breathing gas from the patient circuit to an airway of the patient. Examples of suitable patient interface devices include a nasal mask, nasal/oral mask (which is shown in FIG. 1), nasal prong, full-face mask, tracheal tube, endrotracheal tube, nasal pillow, etc.

Pneumatic system 22 may be configured in a variety of ways. In the present example, system 22 includes an expiratory module 40 coupled with an expiratory limb 34 and an inspiratory module 42 coupled with an inspiratory limb 32. Compressor 44 or another source(s) of pressurized gas (e.g., air and oxygen) is coupled with inspiratory module 42 to provide a gas source for ventilatory support via inspiratory limb 32.

The pneumatic system may include a variety of other components, including sources for pressurized air and/or oxygen, mixing modules, valves, sensors, tubing, accumulators, filters, etc. Controller 50 is operatively coupled with pneumatic system 22, signal measurement and acquisition systems, and an operator interface 52 may be provided to enable an operator to interact with the ventilator (e.g., change ventilator settings, select operational modes, view monitored parameters, etc.). Controller 50 may include memory 54, one or more processors 56, storage 58, and/or other components of the type commonly found in command and control computing devices.

The memory 54 is computer-readable storage media that stores software that is executed by the processor 56 and which controls the operation of the ventilator 20. In an embodiment, the memory 54 comprises one or more solid-state storage devices such as flash memory chips. In an alternative embodiment, the memory 54 may be mass storage connected to the processor 56 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 56. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 50 issues commands to pneumatic system 22 in order to control the breathing assistance provided to the patient by the ventilator. The specific commands may be based on inputs received from an operator, the patient 24, the pneumatic system 22 and sensors, the operator interface 52 and/or other components of the ventilator. In the depicted example, operator interface includes a display 59 that is touch-sensitive, enabling the display to serve both as an input and output device.

Figure 2:
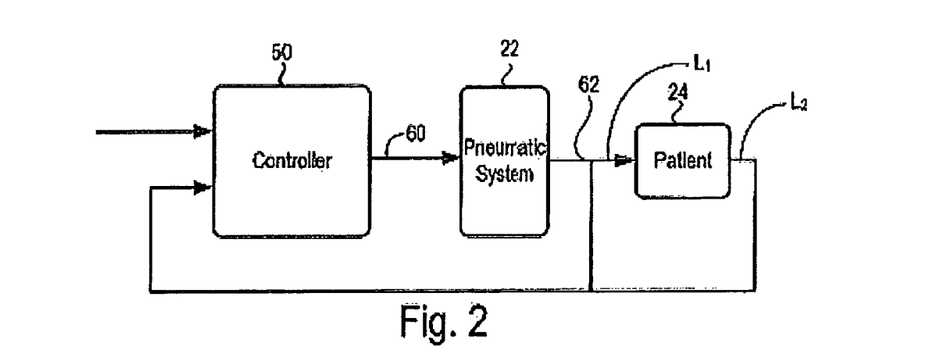
FIG. 2 schematically depicts example systems and methods of ventilator control.

FIG. 2 schematically depicts exemplary systems and methods of ventilator control. As shown, controller 50 issues control commands 60 to drive pneumatic system 22 and thereby circulate breathing gas to and from patient 24. The depicted schematic interaction between pneumatic system 22 and patient 24 may be viewed in terms of pressure and/or flow "signals." For example, signal 62 may be an increased pressure which is applied to the patient via inspiratory limb 32. Control commands 60 are based upon inputs received at controller 50 which may include, among other things, inputs from operator interface 52, and feedback from pneumatic system 22 (e.g., from pressure/flow sensors) and/or sensed from patient 24

In an embodiment, before the respiratory mechanics of a patient can be determined, the mechanics of the ventilation tubing system may be determined. For example, when modeling the delivery of gas to and from a patient 24 via a closed-circuit ventilator, one simple assumption is that compliance of the ventilator circuit 30 (the "circuit compliance") is fixed and that all gas injected into the ventilator circuit 30 that does not exit the circuit 30 via the expiratory limb 34 (in a dual-limb embodiment) fills the circuit as well as the patient's lungs and causes an increase in pressure. As gas is injected ($L_1$), the lung responds to the increased gas pressure in the circuit 30 by expanding. The amount the lung expands is proportional to the lung compliance and is defined as a function of gas pressure differential (e.g., lung compliance=volume delivered/pressure difference). As discussed in greater detail below, this assumption is not valid when leaks are present.

The term circuit compliance is used to refer to the relationship between the pressure in the ventilator circuit 30 (or ventilator circuit 30 and attached patient interface 28, depending on how the compliance is determined) changes based on changes in volume delivered into the circuit. In an embodiment, the circuit compliance may be estimated by pressurizing the ventilator circuit 30 (or circuit 30 and interface 28 combination) when flow to the patient is blocked and measuring the volume of additional gas introduced to cause the pressure change (compliance=volume delivered/pressure difference).

The term circuit resistance is used to refer to the amount the pressure changes between two sites upstream and downstream the ventilator circuit as a function of volumetric flow rate through that circuit. Circuit resistance may be modeled as a two-parameter function of flow and several methods for modeling and calculating circuit resistance are known in the art. For example, in an embodiment the circuit resistance may be estimated by passing several fixed flow rates through the circuit and measuring the pressure difference between certain upstream and downstream sites and finding the best curve fit to the collected data.

Methods of determining circuit compliance and circuit resistance (such as those described above) may be executed by the operator prior to attaching the patient to the ventilator as part of the set up of the ventilator 20 to provide therapy. Other methods of determining circuit compliance and/or resistance during therapy are also known and could be adapted for use with the disclosed leak-compensation systems and methods described herein.

In many cases, it may be desirable to establish a baseline pressure and/or flow trajectory for a given respiratory therapy session. The volume of breathing gas delivered to the patients lung ($L_1$) and the volume of the gas exhaled by the patient ($L_2$) are measured or determined, and the measured or predicted/estimated leaks are accounted for to ensure accurate delivery and data reporting and monitoring. Accordingly, the more accurate the leak estimation, the better the baseline calculation of delivered and exhaled flow rates and volumes.

Errors may be introduced due to leaks in the ventilation tubing system 26. The term ventilation tubing system 26 is used herein to describe the ventilator circuit 30, any equipment attached to or used in the ventilator circuit 30 such as water traps, monitors, drug delivery devices, etc. (not shown), and the patient interface 28. Depending on the embodiment, this may include some equipment contained in the inspiration module 42 and/or the expiration module 40. When referring to leaks in or from the ventilation tubing system 26, such leaks include leaks within the tubing system 26 and leaks where the tubing system 26 connects to the pressure generator 22 or the patient 24. Thus, leaks from the ventilation tubing system 26 include leaks from the ventilator circuit 30, leaks from the patient interface 28 (e.g., masks are often provided with holes or other pressure relief devices through which some leakage may occur), leaks from the point of connection of the patient interface 28 to the patient 24 (e.g., leaks around the edges of a mask due to a poor fit or patient movement), and leaks from the point of connection of the patient interface 28 to the circuit 30 (e.g., due to a poor connection between the patient interface 28 and the circuit 30).

For the purpose of estimating how a leak flow rate changes based on changes in pressure in the ventilation tubing system 26, the instantaneous leak may be modeled as a leak through a single rigid orifice or opening of a fixed size in which that size is determined based on comparing the total flow into the inspiratory limb 32 and out of the expiratory limb 34. However, this leak model does not take into account any elastic component of leak source(s) in the system 26, that is how much of the area of any of the holes or openings in the ventilation tubing system 26 through which leakage occurs may change due to an increase or decrease in pressure.

It has been determined that not accounting for elastic leakage from the ventilation tubing system 26 can cause many problems. First, if only the inelastic/fixed orifice model is used to estimate leak, the subsequent errors caused by ignoring the elastic effects of any actual leaks end up generating inaccurate estimates of flow rates into the lung. This can cause the ventilator 20 to estimate gas volume delivered into the lung inaccurately when, in fact, the elastic leaks in the system 26 have let more gas escape than estimated. Second, if the elasticity of the leak source is ignored, any other calculation, estimate, or action that the ventilator 20 may perform which is affected by the leak estimate will be less accurate.

In the systems and methods described herein, the provision of PRVC ventilation is made more accurate by compensating for leakage from the ventilation tubing system. In the embodiments described herein fixed (rigid) and elastic components of the system leakage are used when determining the lung flow, net lung volume, lung compliance and lung resistance of the patient. This results in a more accurate determination of lung compliance and lung resistance and, therefore, ventilation of patients based on respiratory mechanics. While the systems and methods are presented in the context of specific leakage models, the technology described herein could be used to compensate the respiratory mechanics determined by any model for leakage using any type of mechanical ventilator or other device that provides gas.

Figure 3:
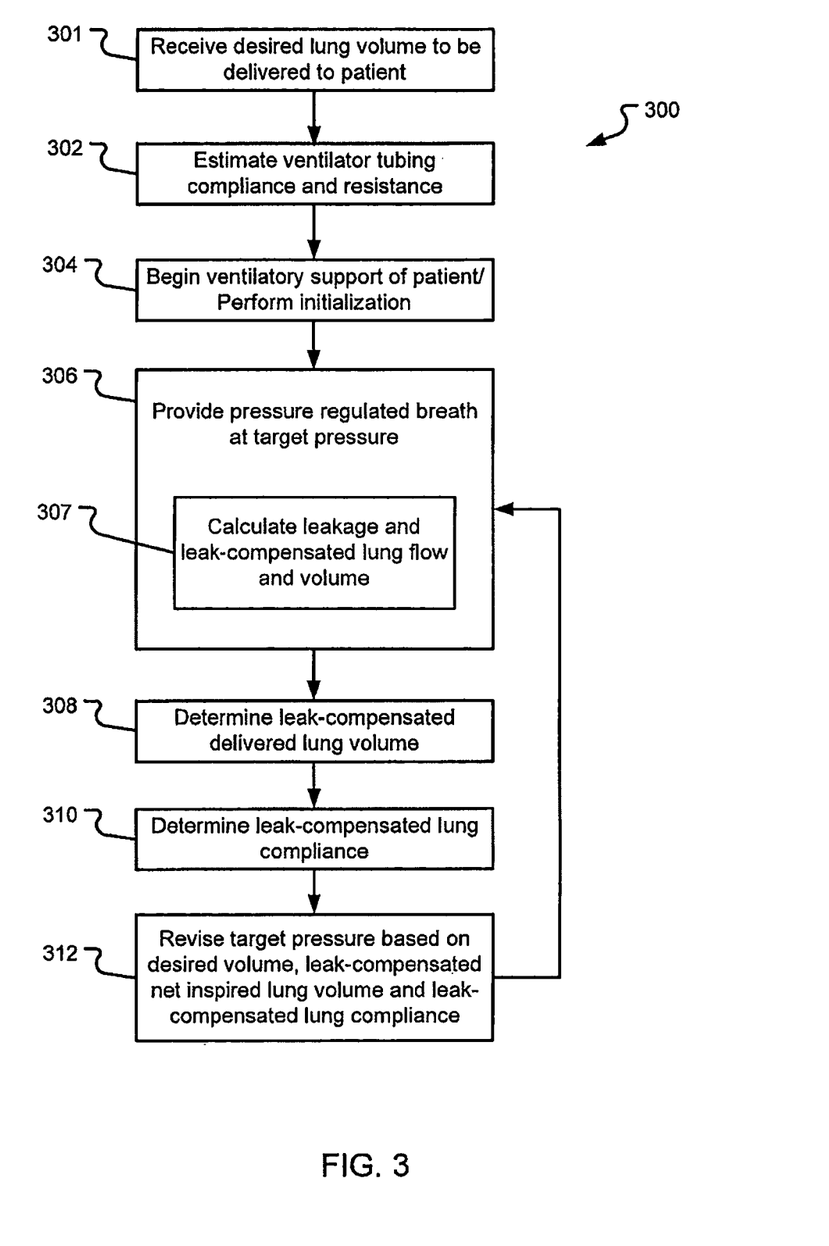
FIG. 3 illustrates an embodiment of a method of compensating for leakage in a ventilator providing pressure-regulated volume control ventilation to a patient.

FIG. 3 illustrates an embodiment of a method of compensating PRVC ventilation for leakage during delivery of gas from a medical ventilator to a patient. In the method 300 shown, a medical ventilator such as that described above with reference to FIGS. 1 and 2 is used to provide PRVC ventilation to a patient.

The method 300 illustrated starts with a setup operation 301 in which the operator directs the ventilator to provide PRVC ventilation. In the setup operation 301, the operator selects a volume of gas to be delivered to the patient, that is to be delivered into the lung, over a specified time period such as a minute, a number of breaths, etc. This desired delivered volume is received by the ventilator and stored in memory for use during PRVC ventilation.

In the embodiment shown, the method 300 includes a circuit compliance and resistance operation 302. In that operation 302, the ventilator circuit compliance and resistance are estimated. In an embodiment, this may be performed prior to connecting the ventilator to the patient (as previously described). Alternatively, it may be dynamically determined periodically throughout the delivery of ventilatory support to the patient. The circuit compliance and resistance may be used in the remaining operations to correct for any losses in volume or effects on the volume delivered to the patient introduced due to the patient circuit.

After the circuit compliance and resistance have been determined, the ventilator is connected to the patient and an initialization operation 304 is performed. In the initialization operation 304 the ventilator operates for an initialization period in order to generate an initial estimate of lung compliance. If the ventilator already has some knowledge of the respiratory mechanics of the patient (e.g., the respiratory mechanics have been recently determined during provision of a different type of ventilation or an operator has provided initial settings for lung compliance and resistance), this operation 304 may be automatically or manually omitted in favor of the previously determined values.

A description of an embodiment of the initialization operation 304 is as follows. Because the ventilator does not know the patient's mechanics when the PRVC breath type is selected, it performs a startup routine to obtain initial data. In an embodiment, upon startup the ventilator delivers some number (e.g., two, four, etc.) of consecutive pressure-based breaths. One or more of these initial breaths given in the startup period may also include an end-inspiratory or other maneuver that yields estimates of the patient's lung compliance. Using four training breaths for the initialization operation 304 as an example, the first breath is delivered using a predicted resistance for the artificial airway and conservative estimates for patient lung compliance. The predicted values may be determined based on known characteristics of the patient, such as based on the patient's ideal body weight (IBW), height, gender, age, physical condition, etc. Each of the following three pressure-based breaths averages stepwise decreased physiologic values with the estimated lung compliance values from the previous breaths, weighting earlier estimates less with each successive breath, and yielding more reliable estimates for lung compliance. Other methods may be used to find a first estimate of the lung compliance and update it on an ongoing basis as ventilation continues.

In an embodiment of the method 300, a leakage estimate may also be done prior to the initialization operation 304. Prior determination of leak parameters allows for estimates of respiratory mechanics to be made. This may include delivering pressure-regulated breaths with specific settings or performing specific "leak maneuvers", that is a specified set of controlled actions on the part of the ventilator that allow leakage parameters to be identified and quantified, such as interrupting the therapeutic delivery of respiratory gas and holding or changing the pressure and flow, so that data concerning the leakage of the system during the controlled actions may be obtained. For example, a leak maneuver may include periodically holding the pressure and flow in the circuit constant while determining (based on a comparison of the measured flow into the inspiratory limb and the measured flow out of the expiratory limb via the exhalation valve) the net leakage from the system. In an embodiment, such a leak maneuver may be performed during specific parts of the respiratory phase, e.g., at the end of the expiratory phase. In yet another embodiment, a sequence of pressure-based test breaths is delivered with specific settings to determine leak parameters prior to execution of test breaths for respiratory mechanics determinations.

After the initialization operation 304, the ventilator provides ongoing PRVC ventilation to the patient in a PRVC ventilation operation 306. As discussed above, during PRVC ventilation the ventilator calculates a target pressure to be delivered to the patient during inspiration based on the desired lung volume to be delivered and the leak-compensated lung compliance of the patient. When in an inspiratory phase, the ventilator raises the pressure in the ventilator tubing system so that the target inspiratory pressure is applied. During exhalation, the pressure may be dropped to some pre-selected positive end expiratory pressure (PEEP) level or to atmospheric level depending on the desires of the operator. The duration of the inspiratory and expiratory phases may be determined based on patient effort or based on a preselected inspiratory time.

As described above, the target pressure delivered during each inspiratory phase is determined based on the desired lung volume to be delivered and leak-compensated lung compliance of the patient. In order to compensate for leakage in the circuit, in the method 300 shown the PRVC ventilation operation 306 includes the ongoing calculation of leakage while providing ventilation, as illustrated by the leakage calculation/compensation operation 307. As discussed in greater detail below with reference to FIG. 4, the leakage is calculated and the leak-compensated values for lung flow and current lung volume (i.e., the volume of gas in the lung at that moment) are determined taking into account the calculated leakage.

The method 300 also includes determining the leak-compensated delivered lung volume in a delivered volume calculation operation 308. The delivered volume calculation operation 308 uses the leak-compensated lung flow and net lung volume to determine how much gas was delivered to the lungs of the patient during the breath. In an embodiment, this operation 308 is an ongoing operation in which the volume of gas delivered to the patient is accumulated over the course of the inspiratory phase, so that upon completion of the inspiratory phase the accumulated volume is the total delivered volume for the breath. Alternatively, this operation 308 may be performed as soon as the inspiratory phase ends, any time during the expiratory phase or at the beginning of the next inspiratory phase using leak-compensated lung flow or volume data collected during the breath.

The leak-compensated delivered lung volume for the breath is then used in a lung compliance calculation operation 310 to calculate a leak-compensated lung compliance for the patient. In an embodiment, the lung compliance calculation operation 310 includes using the following equation to determine lung compliance:

$$\text{Leak-Compensated Lung Compliance} = V/(EIP-EEP)$$

in which V is the leak-compensated delivered lung volume for the breath, EIP is the pressure at the end of the inspiratory phase of the breath, and EEP is the pressure at the end of the expiratory phase of the breath. As mentioned above, these pressure values are determined from the monitoring of pressure and/or flow during the PRVC ventilation operation 306.

The above equation is but one example of a method of determined lung compliance from parameters monitored by a ventilator such as pressure, flow and volume. Any suitable method may be used as long as the monitored parameters are compensated for the leakage identified in the leakage calculation/compensation operation 307 so that a leak-compensated lung compliance is obtained.

In an embodiment, the delivered volume calculation operation 308 and lung compliance calculation operation 310 may be performed as a single operation at the same time instead of separately as shown.

Based on the leak-compensated lung compliance, the system then calculates a target pressure for the next breath in a calculate target pressure operation 312. This calculation takes into account the leak-compensated volume of gas delivered to the patient's lungs during the last breath to determine if sufficient volume is being delivered relative to the desired volume identified by the operator. This calculation also may take into account the leak-compensated volume of gas delivered during earlier breaths depending on the time period over which the desired volume is to be delivered. Depending on the comparison of the leak-compensated delivered lung volume and the desired delivered lung volume, the target pressure to be used for the next breath may be raised or lowered relative to the current pressure. The amount the target pressure is raised or lowered is a function of the leak-compensated lung compliance, the predicted or known inspiratory phase duration and ventilator settings as well as patient safety precautions.

The newly determined values of lung compliance and lung resistance may be averaged, low-pass filtered or otherwise combined with the previously determined values. These revised values are then stored for use in later delivery of PRVC ventilation.

In an embodiment, the delivered volume calculation operation 308, lung compliance calculation operation 310 and calculate target pressure operation 312 may be performed as a single operation at the same time instead of separately as shown.

After calculating the revised target pressure, upon the next inspiration the ventilator then provides the revised target pressure to the patient, illustrated in FIG. 3 by the flow returning to the PRVC ventilation operation 306. The method 300 is then repeated from that point until the delivery of PRVC ventilation is terminated by some outside action, such as, change of mode setting or failure to converge on an acceptable lung compliance value.

Figure 4:
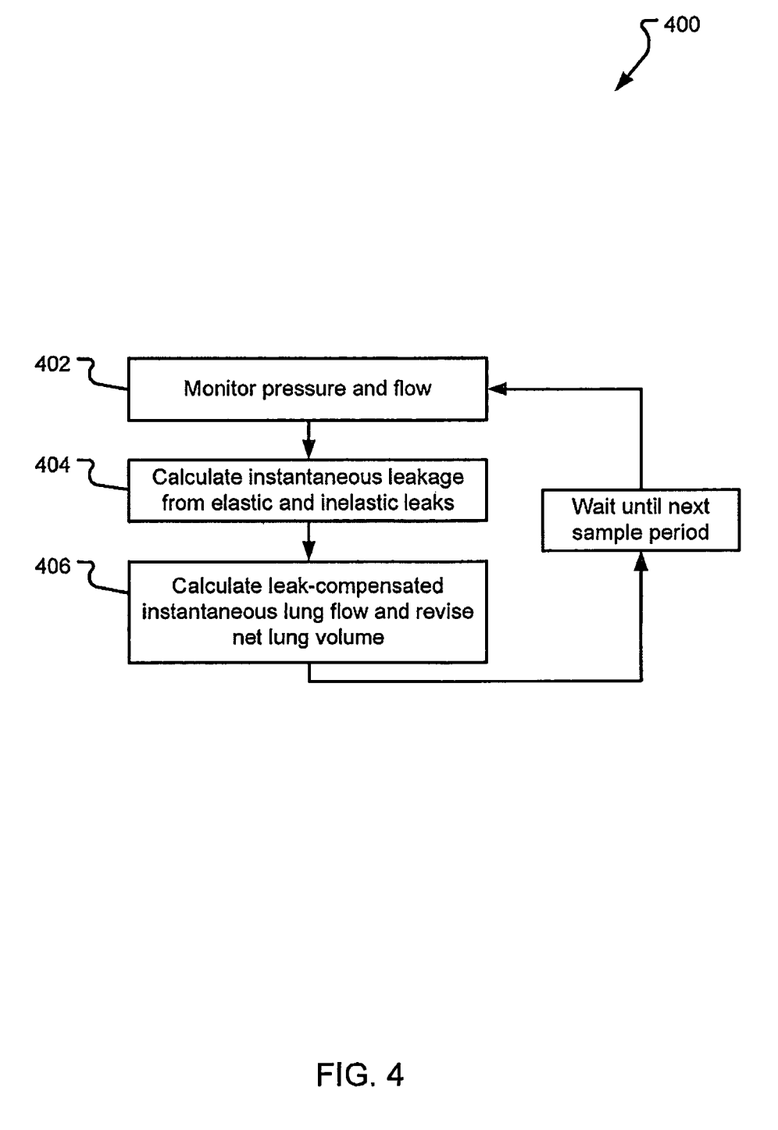
FIG. 4 illustrates an embodiment of a method for calculated leak-compensated lung flow and delivered lung volume while providing pressure-regulated volume control ventilation to a patient.

FIG. 4 illustrates an embodiment of a method for calculating leak-compensated parameters while providing PRVC ventilation to a patient. In an embodiment, the method 400 corresponds to the operations performed during the leakage determination operation 306 discussed with reference to FIG. 3. In the embodiment of the method 400 illustrated, the operations occur repeatedly while the ventilator is providing PRVC ventilation, such as once a sample period or computation cycle, while the ventilator is providing either the target pressure (during the inspiratory phase) or an expiratory pressure such as PEEP (during the expiratory phase).

During PRVC ventilation, the pressure and flow and other parameters of the system are monitored, illustrated by the monitoring operation 402. In an embodiment, the monitoring operation 402 collects data including the instantaneous pressure and/or flow at or indicative of one or more locations in the ventilation tubing system. Depending upon how a particular leak model is defined, the operation 402 may also include making one or more calculations using data from pressure and flow measurements taken by the sensors. For example, a model may require a flow measurement as observed at the patient interface even though the ventilation system may not have a flow sensor at that location in the ventilation tubing system. Thus, a measurement from a sensor or sensors located elsewhere in the system (or data from a different type of sensor at the location) may be mathematically manipulated in order to obtain an estimate of the flow observed at the patient interface in order to calculate the leak using the model.

The data obtained in the monitoring operation 402 is then used to calculate leakage from the ventilator tubing system in a leakage calculation operation 404. In an embodiment) the leakage calculation operation 404 uses the data obtained in the monitoring operation 402, e.g., some or all of the instantaneous pressure and flow data collected during the monitoring operation 402 as well as information about the current respiratory phase (inhalation or exhalation).

The leakage calculation operation 404 calculates an instantaneous leakage flow or volume for the sample period. The instantaneous leakage is calculated using a mathematical formula that has been previously determined. In an embodiment, the mathematical formula is a leakage model that separates the leak into the sum of two leak components, inelastic leak and elastic leak, in which each component represents a different relationship between the quantity of leakage from the ventilation system and the measured current/instantaneous pressure and/or flow of gas in the ventilation system. As discussed above, the inelastic leak may be modeled as the flow through a rigid orifice of a fixed size while the elastic leak may be modeled as the flow through a different orifice of a size that changes based on the pressure (or flow) of the gas in the ventilation system.

An example of a method and system for modeling leak in a ventilation system as a combination of an elastic leak component and an inelastic leak component can be found in commonly-assigned U.S. Provisional Patent Application Ser. No. 61/041,070, filed Mar. 31, 2008, titled VENTILATOR LEAK COMPENSATION, which application is hereby incorporated by reference herein. The VENTILATOR LEAK COMPENSATION represents one way of characterizing the leak from a ventilation system as a combination of elastic and inelastic components. Other methods and models are also possible and may be adapted for use with this technology.

The mathematical formula used to calculate leakage may contain several parameters that are empirically determined and that may be periodically or occasionally revised in order to maintain the accuracy of the leakage estimate. For example, in an embodiment the parameters of a leakage formula include a first constant associated with the rigid orifice and a second constant associated with the variable-sized orifice. At various times during ventilation, the calculated leakage may be checked against a measured leakage and, if the estimate is significantly different from the measured leakage, the constants may be revised. This revision of the parameters in a leakage formula may be done as part of the leakage calculation operation 404 or may be done as a separate operation (not shown) that may, or may not, be performed every sample period.

The term instantaneous is used herein to describe a determination made for any particular instant or sampling period based on the measured data for that instant. For example, if a pressure measurement is taken every 5 milliseconds (sample period), the pressure measurement and the leak model can be used to determine an instantaneous leak flow based on the instantaneous pressure measurement. With knowledge of the length of the sample period, the instantaneous flow may then be used to determine an instantaneous volume of gas leaking out of the circuit during that sample period. For longer periods covering multiple sample periods the instantaneous values for each sample period may be summed to obtain a total leakage volume. If a measurement is also the most recent measurement taken, then the instantaneous value may also be referred to as the current value.

After the current leak has been calculated, the method 400 further estimates the leak-compensated instantaneous lung flow to or from the patient in a lung flow estimation operation 406. The estimated lung flow is compensated for the leak flow calculated in the instantaneous leak calculation operation 404 so that it represents a more accurate estimate of the actual flow into (or out of depending on the point of view and period selected) the lungs of the patient.

In the embodiment illustrated, the leak-compensated net and delivered lung volumes are also calculated as part of the lung flow estimation operation 406. In an embodiment, this may be performed by maintaining a running summation of net flow into/out of the lung over the period of a breath and a running summation of the flow delivered to the patient during the inspiratory phase. For example, upon triggering inhalation, the ventilator may set a variable corresponding to net lung volume to zero and, each sample period, update this net lung volume to include the detected leak-compensated instantaneous lung flow delivered to the patient during that sample period. Likewise, the ventilator may also set a variable corresponding to delivered lung volume to zero and, each sample period during the inspiratory phase, update this net lung volume to include the detected leak-compensated instantaneous lung flow into the patent, if any, during that sample period.

In the PRVC ventilation method 400 illustrated, the leak-compensated lung flow or delivered lung volume will ultimately be used to calculate a leak-compensated lung compliance as described in FIG. 3. Ultimately, this leak-compensated lung compliance along with other leak-compensated data will be used to determine the target pressure for the next inspiratory phase.

The method 400 is then repeated every computational cycle or sample period, as illustrated by the feedback loop, so that the leak-compensated instantaneous lung flow and leak-compensated delivered lung flow are continuously determined during PRVC ventilation.

The following is a discussion of two embodiments of methods for compensating the estimation of respiratory mechanics for leaks. The first embodiment is that of applying leak compensation to a static compliance and resistance determination. The second embodiment is that of applying leak compensation to a dynamic compliance determination.

Figure 5:
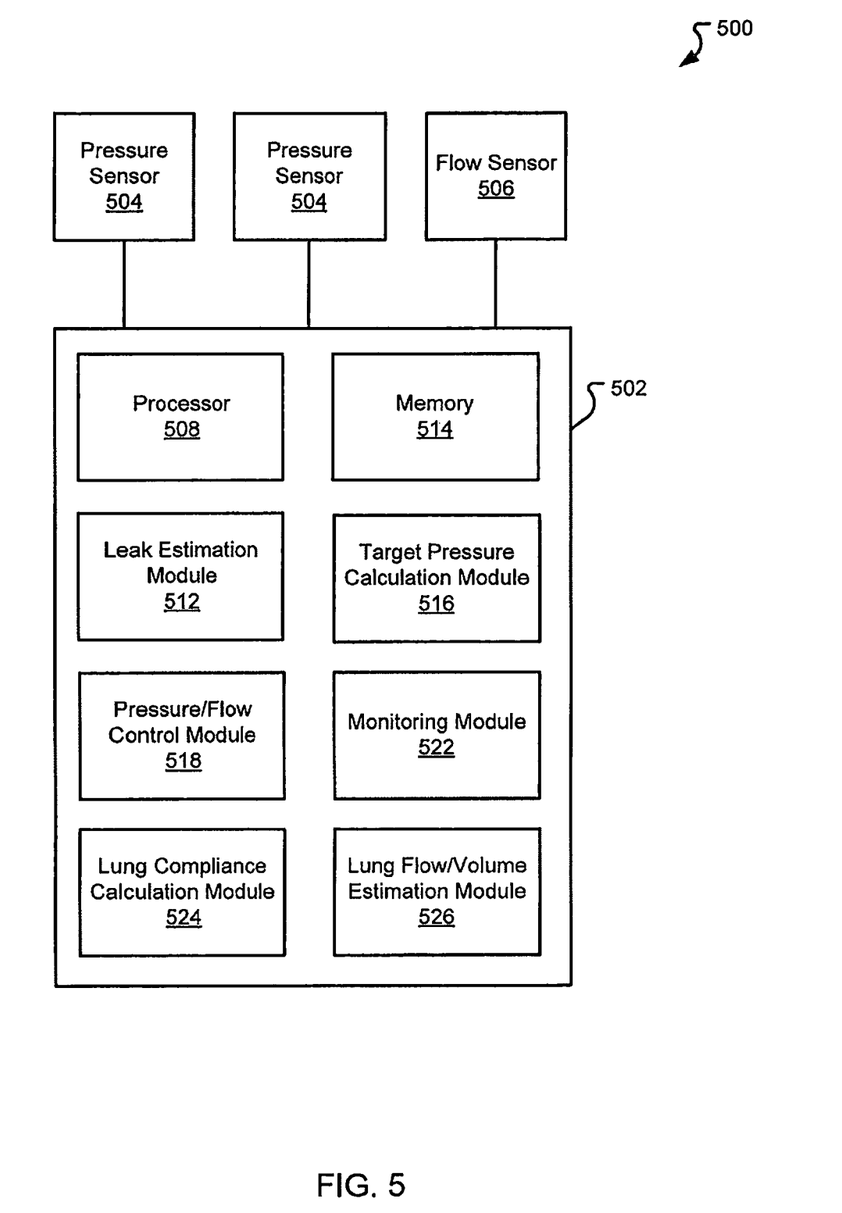
FIG. 5 illustrates a functional block diagram of modules and other components that may be used in an embodiment of ventilator that compensates for elastic and rigid orifice sources of leaks when determining the target pressure during pressure-regulated volume control ventilation.

FIG. 5 illustrates a functional block diagram of modules and other components that may be used in an embodiment of ventilator that compensates for elastic and rigid orifice sources of leaks when determining the target pressure during PRVC ventilation. In the embodiment shown, the ventilator 500 includes pressure sensors 506 (two are shown placed at different locations in the system), flow sensors (one is shown), and a ventilator control system 502. The ventilator control system 502 controls the operation of the ventilator and includes a plurality of modules described by their function. In the embodiment shown, the ventilator control system 502 includes a processor 508, memory 514 which may include mass storage as described above, a leak estimation module 512 incorporating a parametric leak model accounting for both elastic and rigid orifice leak sources such as that described in U.S. Provisional Application 61/041,070 previously incorporated herein, a target pressure calculation module 516, a pressure and flow control module 518, a monitoring module 522, a leak-compensated lung compliance module 524, and a leak-compensated lung flow and volume estimation module 526. The processor 508 and memory 514 have been discussed above. Each of the other modules will be discussed in turn below.

The main functions of the ventilator such as receiving and interpreting operator inputs and providing therapy via changing pressure and flow of gas in the ventilator circuit are performed by the control module 518. In the context of the methods and systems described herein, the module 518 will perform one or more actions upon the determination that a patient receiving therapy is inhaling or exhaling.

In the embodiment described herein, the control module 518 determines and provides the appropriate pressure to the patient when in PRVC ventilation mode. This may include performing one or more calculations based on leak-compensated lung flow, leak-compensated lung volume, leak-compensated lung compliance and leak-compensated lung resistance.

The calculation of the target pressure to provide during the inspiratory phase of a breath is performed by the target pressure calculation module 516. The target pressure is calculated based on the therapist-selected desired lung volume and the leak-compensated delivered lung volume. The module 516 utilizes one or more respiratory models suitable for determination of target pressure based on monitored parameters and/or leak-compensated respiratory mechanics such as lung compliance. The module 516 uses leak-compensated values for one or both of lung flow and delivered lung volume when calculating the target pressure, depending on the method used by the module. Leak-compensated values may be retrieved if they have already been calculated or may be calculated as needed from leakage information received from the leak-compensated lung flow and net lung volume estimation module 526.

The dynamic calculation of lung compliance is performed by the leak-compensated lung compliance calculation module 524. The module 524 utilizes one or more dynamic respiratory models, such as that described above with reference to lung compliance calculation operation 310 of FIG. 3, to calculate leak-compensated lung compliance. The module 524 uses leak-compensated values for one or both of lung flows and delivered lung volume when calculating lung compliance. Leak-compensated values may be retrieved if they have already been calculated or may be calculated from leakage information received from the leak-compensated lung flow and delivered lung volume estimation module 526.

The current conditions in the ventilation system are monitored by the monitoring module 522. This module 522 collects the data generated by the sensors 504, 506 and may also perform certain calculations on the data to make the data more readily usable by other modules or may process the current data and or previously acquired data or operator input to derive auxiliary parameters or attributes of interest. In an embodiment, the monitoring module 522 receives data and provides it to each of the other modules in the ventilator control system 502 that need the current pressure or flow data for the system.

In the embodiment shown, leak-compensated lung flow and delivered lung volume are calculated by the lung flow module 526. The lung flow module 526 uses a quantitative model for lung flow of the patient during both inhalation and exhalation and from this characterization and pressure and flow measurements generates an estimate for instantaneous lung flow. In an embodiment, lung flow may be simply determined based on subtracting the estimated leak flow and measured outflow via the expiratory limb from the flow into the inspiratory limb, thereby generating a leak-compensated net flow into (or out of) the lung. The lung flow module 526 may or may not also calculate a leak-compensated delivered lung volume for a patient's breath as described above. Compression in the circuits and accessories may also be accounted for to improve the accuracy of estimated lung flow.

The leak model parameters are generated by the leak estimation module 512 which creates one or more quantitative mathematical models, equations or correlations that uses pressure and flow observed in the ventilation system over regular periods of respiratory cycles (inhalation and exhalation) and apply physical and mathematical principles derived from mass balance and characteristic waveform settings of ventilation modalities (regulated pressure or flow trajectories) to derive the parameters of the leak model incorporating both rigid and elastic (variable pressure-dependent) orifices. In an embodiment, the mathematical model may be a model such as:

$$Q_{inelastic} = R_1 * P_i^x$$

$$Q_{elastic} = R_2 * P_i^y$$

wherein $Q_{elastic}$ is the instantaneous leak flow due to elastic leaks in the ventilation system, $Q_{inelastic}$ is the instantaneous leak flow due to inelastic leaks in the ventilation system, $R_1$ is the inelastic leak constant, $R_2$ is the elastic leak constant, $P_i$ is the current or instantaneous pressure measurement, x is an exponent for use when determining the inelastic leak and y is an exponent different than x for use when determining the elastic leak. The group $R_1 * P_i^x$ represents flow through an orifice of fixed size as a function of instantaneous pressure $P_i$ and the group $R_2 * P_i^y$ represents flow through a different orifice that varies in size based on the instantaneous pressure. The equations above presuppose that there will always be an elastic component and an inelastic component of leakage from the ventilation system. In the absence of an elastic component or a leak source of varying size, $R_2$ would turn out be zero.

In the embodiment shown, the current or instantaneous elastic leak is calculated by the leak estimation module 512. The calculation is made using the elastic leak portion of the leak model developed by the leak estimation module 512 and the pressure data obtained by the monitoring module 522. The leak estimation module 512 may calculate a new instantaneous elastic leak flow or volume for each pressure sample taken (i.e., for each sampling period) by the monitoring module 522. The calculated elastic leak may then be provided to any other module as needed.

In the embodiment shown, the current or instantaneous inelastic leak is also calculated by the leak estimation module 512. The calculation is made using the inelastic leak portion of the leak model and the pressure data obtained by the monitoring module 522. The leak estimation module 512 may calculate a new instantaneous inelastic leak flow or volume for each pressure sample taken (i.e., for each sampling period) by the monitoring module 522. The calculated inelastic leak may then be provided to any other module as needed.

The system 500 illustrated will compensate lung flow for leaks due to elastic and inelastic leaks in the ventilation system. Furthermore, the system may perform a dynamic compensation of lung flow based on the changing leak conditions of the ventilation system and the instantaneous pressure and flow measurements. The system then compensates the lung compliance and target pressure calculations based on the estimated leakage in the system. By compensating for the inelastic as well as the elastic components of dynamic leaks, the medical ventilator can more accurately and precisely a target pressure so that the desired lung volume selected by the therapist is achieved.

Furthermore, embodiments of the systems and methods described above may also include checks and balances based on patient type and known characteristics (e.g., Ideal Body Weight, etc.). For example, a calculated pressure target (or change between the current and the newly calculated pressure target to be used in the next inspiration) may be compared against a safety criteria based on Ideal Body Weight, age, gender patient parameters determined during ventilation or operator provided safety thresholds.

If the comparison indicates the newly calculated pressure is unsafe, the ventilator may perform one or more safety actions. In an embodiment, such safety actions may include limiting stepwise changes in desired pressure target and generating alarms or warnings. Delivery of PRVC may also be terminated in situations deemed unsafe for the patient or when acceptable data are not available (e.g, when the process of lung compliance estimation fails to converge to an acceptable value). In such a situation the ventilator may switch to some other mode, such as a pressure support mode or volume control mode, than PRVC. The mode switched may be determined by the operator when setting up the PRVC ventilation or may be a default mode selected by the manufacturer.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. For example, the operations and steps of the embodiments of methods described herein may be combined or the sequence of the operations may be changed while still achieving the goals of the technology. In addition, specific functions and/or actions may also be allocated in such as a way as to be performed by a different module or method step without deviating from the overall disclosure. In other words, functional elements being performed by a single or multiple components, in various combinations of hardware and software, and individual functions can be distributed among software applications. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the technology described herein. For example, the systems and methods described herein could be adapted to periodically perform a static respiratory mechanics maneuver to obtain a more accurate lung compliance estimate in order to check the dynamically determined leak-compensated lung compliance Numerous other changes may be made which will readily suggest themselves to those skilled in the art and which are encompassed in the spirit of the disclosure and as defined in the appended claims.

What is claimed is:

1. A method of compensating for leakage in a ventilation system during delivery of pressure regulated volume control ventilation to a patient, the method performed by the ventilation system, the method comprising:
monitoring an instantaneous flow in the ventilation system based on one or more measurements of pressure and flow in ventilation system;
modeling, by the ventilation system, leakage as a first leakage component through a first orifice of a fixed size and a second leakage component through a second orifice of a varying size, wherein the first and second leakage components are different functions of instantaneous pressure in the ventilation system;

estimating a leak-compensated delivered lung volume for at least one breath based on the one or more measurements, the first leakage component and the second leakage component;

using the leak-compensated delivered lung volume and a predetermined respiratory mechanics model to estimate a leak-compensated lung compliance; and calculating a target pressure to be delivered to the patient for a subsequent breath based on a desired lung volume, the leak-compensated delivered lung volume and the leak-compensated lung compliance.

2. The method of claim 1 further comprising:
estimating the leak-compensated lung compliance based on the leak-compensated delivered lung volume and a pressure difference.

3. The method of claim 2 wherein the pressure difference is a difference between an end inspiratory pressure of a first breath and an end expiratory pressure of the first breath.

4. The method of claim 1 wherein the method further comprises:
calculating the target pressure based on a difference between the desired lung volume and the leak-compensated delivered lung volume.

5. The method of claim 1 wherein the method further comprises:
determining a circuit compliance of ventilation system; and
estimating a leak-compensated delivered lung volume for at least one breath based on the one or more measurements, the circuit compliance, the first leakage component and the second leakage component.

6. The method of claim 1 wherein the method further comprises:
upon initiation of pressure regulated volume control ventilation, calculating an initial lung compliance from data obtained during a startup period; and
determining an initial target pressure to be delivered to the patient for at least one breath after the startup period.

7. A method of compensating for leakage in a ventilation tubing system during delivery of gas from a medical ventilator to a patient, the method performed by the medical ventilator, the method comprising:
measuring leakage from the ventilation tubing system during a first breath;
calculating, by the medical ventilator., a leak-compensated delivered lung volume for the first breath based on the leakage;
estimating a lung compliance of the patient based on the leak-compensated delivered lung volume and pressure measurements taken during the first breath; and
delivering ventilation to the patient in a second breath at a pressure determined based on a desired delivered lung volume, the leak-compensated delivered lung volume and the leak-compensated lung compliance.

8. The method of claim 7 wherein measuring leakage further comprises:
identifying an inelastic leakage from the ventilation tubing system as a first function of at least one of a pressure measurement and a flow measurement in the ventilation system; and
identifying an elastic leakage from the ventilation tubing system as a second function of at least one of the pressure measurement and the flow measurement in the ventilation system.

9. The method of claim 7 wherein calculating the leak-compensated delivered lung volume further comprises:
generating a plurality leak-compensated lung flows each associated with a different period of time within the first breath;
generating the leak-compensated delivered lung volume for the first breath based on the leak-compensated lung flows.

10. The method of claim 7 wherein estimating the lung compliance further comprises:
receiving the desired lung volume from an operator.

* * * * *